(12) United States Patent
Jinton et al.

(10) Patent No.: US 11,882,409 B2
(45) Date of Patent: Jan. 23, 2024

(54) BONE ANCHOR FIXTURE FOR A MEDICAL PROSTHESIS

(71) Applicants: Lars Jinton, Molndal (SE); Erik Holgersson, Gothenburg (SE); Peter Elmberg, Kallered (SE)

(72) Inventors: Lars Jinton, Molndal (SE); Erik Holgersson, Gothenburg (SE); Peter Elmberg, Kallered (SE)

(73) Assignee: Cochlear Limited, Macquarie University (AU)

( * ) Notice: Subject to any disclaimer, the term of this patent is extended or adjusted under 35 U.S.C. 154(b) by 466 days.

(21) Appl. No.: 16/985,808

(22) Filed: Aug. 5, 2020

(65) Prior Publication Data

US 2021/0058721 A1 Feb. 25, 2021

Related U.S. Application Data

(63) Continuation of application No. 15/830,616, filed on Dec. 4, 2017, now Pat. No. 10,750,297, which is a continuation of application No. 14/922,604, filed on Oct. 26, 2015, now Pat. No. 9,838,807, which is a continuation of application No. 12/177,083, filed on Jul. 21, 2008, now Pat. No. 9,173,042.

(60) Provisional application No. 60/951,163, filed on Jul. 20, 2007, provisional application No. 60/951,169, filed on Jul. 20, 2007.

(51) Int. Cl.
*A61B 17/86* (2006.01)
*H04R 25/00* (2006.01)
*A61C 8/00* (2006.01)

(52) U.S. Cl.
CPC ......... *H04R 25/606* (2013.01); *A61B 17/863* (2013.01); *A61B 17/8615* (2013.01); *A61C 8/0025* (2013.01); *A61C 8/0066* (2013.01); *A61C 8/0069* (2013.01); *H04R 2460/13* (2013.01)

(58) Field of Classification Search
CPC ..................................................... H04R 25/606
See application file for complete search history.

(56) References Cited

U.S. PATENT DOCUMENTS

| 5,571,017 A * | 11/1996 | Niznick | ............... A61C 8/0022 433/173 |
| 2006/0093175 A1 * | 5/2006 | Westerkull | ........... H04R 25/606 381/326 |

* cited by examiner

*Primary Examiner* — Christian A Sevilla
(74) *Attorney, Agent, or Firm* — Pilloff Passino & Cosenza LLP; Martin J. Cosenza

(57) ABSTRACT

A screw-shaped anchoring fixture for anchoring a prosthesis in the skull bone. The anchoring fixture comprises a main body configured to be implanted into the bone and a flange configured to function as a stop to prevent the main body from completely penetrating through the bone. The main body comprises a distal tapered apical portion, a first portion, and a second portion. The inner diameter of the second portion is greater than the inner diameter of the first portion. The method for inserting the anchoring fixture includes providing the anchoring fixture, drilling a hole, and inserting the anchoring fixture into the hole until the flange contacts the skull bone, wherein the hole has a diameter that is greater than the inner diameter of the first portion and less than the outer diameter of the second portion.

26 Claims, 2 Drawing Sheets

BONE ANCHOR FIXTURE FOR A MEDICAL PROSTHESIS

CROSS-REFERENCE TO RELATED APPLICATIONS

The present application is a Continuation application of U.S. patent application Ser. No. 15/830,616, filed Dec. 4, 2017, naming Lars Jinton as an inventor, which is a Continuation application of U.S. patent application Ser. No. 14/922,604, filed Oct. 26, 2015, now U.S. Pat. No. 9,838,807, which is a Continuation application of U.S. patent application Ser. No. 12/177,083, filed Jul. 21, 2008, now U.S. Pat. No. 9,173,042, which claims the benefit of U.S. Provisional Application No. 60/951,163, filed Jul. 20, 2007, and U.S. Provisional Application No. 60/951,169, filed Jul. 20, 2007. The entire contents of these applications are incorporated herein by reference in their entirety.

BACKGROUND

Filed of the Invention

The present invention relates generally to hearing devices and, more particularly, to anchoring elements for bone anchored hearing devices.

Related Art

For persons who cannot benefit from traditional, air conduction hearing aids there are other types of hearing aids on the market commonly referred to as bone anchored hearing aids. Bone anchored hearing aids mechanically transmit sound information to a person's inner ear via the skull bone by means of a vibrator. Such hearing aid devices are typically connected to a percutaneous implant in the form of a titanium screw implanted in the skull bone behind the external ear so that sound is transmitted via the skull bone to the cochlea (inner ear). This enables the hearing aid to be effective regardless of whether there is disease or damage in the middle ear. Moreover, penetration of the skin makes the vibratory transmission very efficient.

Bone anchored hearing aids were initially developed to rehabilitate certain types of hearing-impaired patients. They may also be utilized for other indications such as stuttering and for certain non-medical applications. A bone anchored hearing aid may be connected to an implant by means of a bayonet coupling, a snap-in coupling, a magnetic coupling or the like. One example of this type of hearing aid device is the BAHA® bone anchored hearing aid, described in U.S. Pat. No. 4,498,461 and commercially available from Cochlear Bone Anchored Solutions AB (previously Entific Medical Systems AB) in Göteborg, Sweden.

The implant connecting the hearing aid to the skull generally comprises two components: a bone attachment piece that is attached or implanted directly into the skull bone and a skin penetrating piece coupled to the bone attachment piece. The reason for this two-piece design is that installation of the implant is occasionally performed in two steps. In the first step, the bone attachment piece is installed and the surrounding issue is allowed to heal for a period of time that may last up to a few months. In the second step, the skin penetrating piece is coupled to the bone attachment piece. In the event that the skin penetrating piece becomes damaged, it may be replaced without removing the anchoring fixture from the skull. Moreover, the hearing aid may be changed or upgraded if necessary, without removing the bone attachment piece from the skull.

Although conventional fixtures normally provide a certain degree of osseo-integration, a more effective integration between the implant screw and the skull bone is desired, for example, for patients having impaired bone quality. Moreover, loading of the implant at an earlier stage would also be desired.

SUMMARY

In one embodiment, an anchoring fixture for anchoring a prosthesis to a skull bone is disclosed. The anchoring fixture comprises a main body configured to be implanted into the skull bone. The main body further comprises a distal tapered apical portion and a first portion adjacent to the distal tapered apical portion. The main body also comprises a second portion adjacent to the first portion. The first portion has a first inner diameter and the second portion has a second inner diameter that is greater than the first inner diameter. This configuration provides compression in the radial direction on the skull bone to improve the initial stability of the anchoring fixture.

In another embodiment, an anchoring fixture for anchoring a prosthesis to a skull bone is disclosed. The anchoring fixture comprises a main body configured to be implanted into the skull bone and a flange. The main body further comprises a distal tapered apical portion and a first threaded portion having a first diameter adjacent to the distal apical portion and an adjacent second threaded portion having a second diameter. The second diameter is greater than the first diameter. The flange is adjacent to the second threaded portion, the flange comprising a planar bottom surface adapted to rest on top of the skull bone when the main body is implanted into the skull bone.

In yet another embodiment, an anchoring fixture for anchoring a prosthesis to a skull bone is disclosed. The anchoring fixture comprises an implantation means for securing the anchoring fixture onto the skull bone without completely penetrating through the skull bone. The implantation means comprises a compression means for exerting a compression onto the skull bone in a radial direction to stabilize the fixture in the skull bone.

In a further embodiment, a method for installing the anchoring fixture into a skull bone is disclosed. The method comprises providing an anchoring fixture, drilling a hole into the skull bone and inserting the anchoring fixture in the hole until the flange contacts the skull bone, wherein the hole has a diameter that is greater than the inner diameter of the first portion and less than the outer diameter of the second portion. In one aspect of the embodiment, the inserting step comprises screwing the anchoring fixture into the skull bone.

BRIEF DESCRIPTION OF THE DRAWINGS

Embodiments of the present invention are described herein with reference to the accompanying drawings, in which.

Like numerals refer to like parts throughout the several views of the drawings.

DETAILED DESCRIPTION OF THE INVENTION

Aspects of the various embodiments disclosed herein are generally directed to providing screw-shaped anchoring fixtures configured to be anchored in the comparatively thin skull bone and having a certain compressive ability in the radial direction to improve the initial stability of the fixture.

In one embodiment, the anchoring fixture has a main body configured to be inserted in the skull bone and a flange configured to prevent the fixture from completely penetrating through the skull bone. The main body comprises a first and second substantially cylindrical portion. The first portion comprises a screw thread having a first inner diameter and the second portion is adjacent to the flange and has a second inner diameter that is greater than the first inner diameter. Preferably, the second portion has at least one groove extending around the periphery of the cylindrical portion. The groove may have a bottom diameter exceeding the first inner diameter of the screw thread. Preferably, the groove forms a second screw thread having an inner diameter exceeding the inner diameter of the first, main screw thread. The surface of at least the first portion of the main body may be modified to increase the surface roughness.

In another embodiment, a method for inserting the anchoring fixture is disclosed. In accordance with one aspect of this embodiment, a drill may be used to drill a hole in the skull bone before installing the anchoring fixture. The drill creates a hole in the skull bone having a diameter which is larger than the inner diameter of the screw thread of the first cylindrical portion, but less than the outer diameter of the second cylindrical portion. When the fixture is inserted into the drilled hole, the wider second portion of the fixture, i.e. the portion next to the flange, provides a certain compression to the bone, specifically the cortical bone, in the radial direction of the hole.

Figure 1:
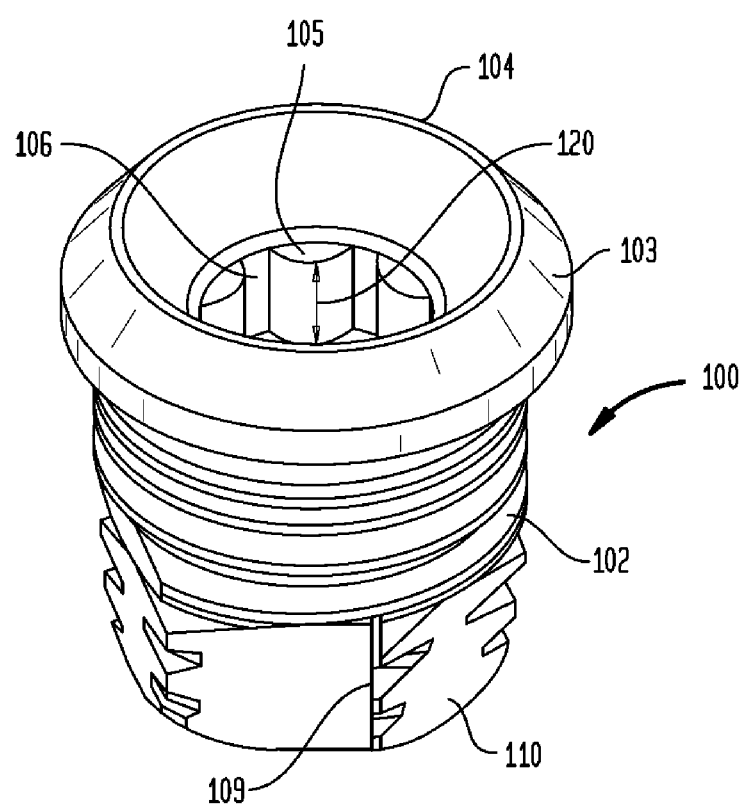
FIG. 1 is a perspective view of an anchoring element in accordance with one embodiment of the anchoring fixture.

Embodiments of the bone anchored coupling apparatus will be described below with reference to the accompanying drawings. FIG. 1 illustrates an example of a screw-shaped anchoring fixture 100 in accordance with one embodiment. Fixture 100 is preferably made of any biocompatible material that has a known ability to integrate with the surrounding bone tissue, a phenomenon commonly referred to as osseointegration. In one embodiment, fixture 100 is made of titanium. Fixture 100 has a main body 102 configured to be implanted into the skull bone, a flange 103 configured to serve as a stop to prevent fixture from penetrating through the skull bone, and a tool engaging socket 104 in the form of an internal grip section 105 for easy lifting and handling of fixture 100. The geometrical configuration of the internal grip section may be configured in a manner that allows for engagement with an insertion tool. In accordance with one aspect, the geometric configuration may be in the form of a hex, multi-lobed surfaces, slots or grooves. As shown in FIG. 1 a number of lobe-shaped surfaces 106 is provided in the internal grip section and extends a distance or height (H) 120 in the longitudinal direction of the main body of the fixture parallel to longitudinal axis 107 of the fixture. The lobe-shaped surfaces 106 may be configured to cooperate with an insertion tool having slightly tapered engaging surfaces to engage and lift the fixture.

Figure 2:
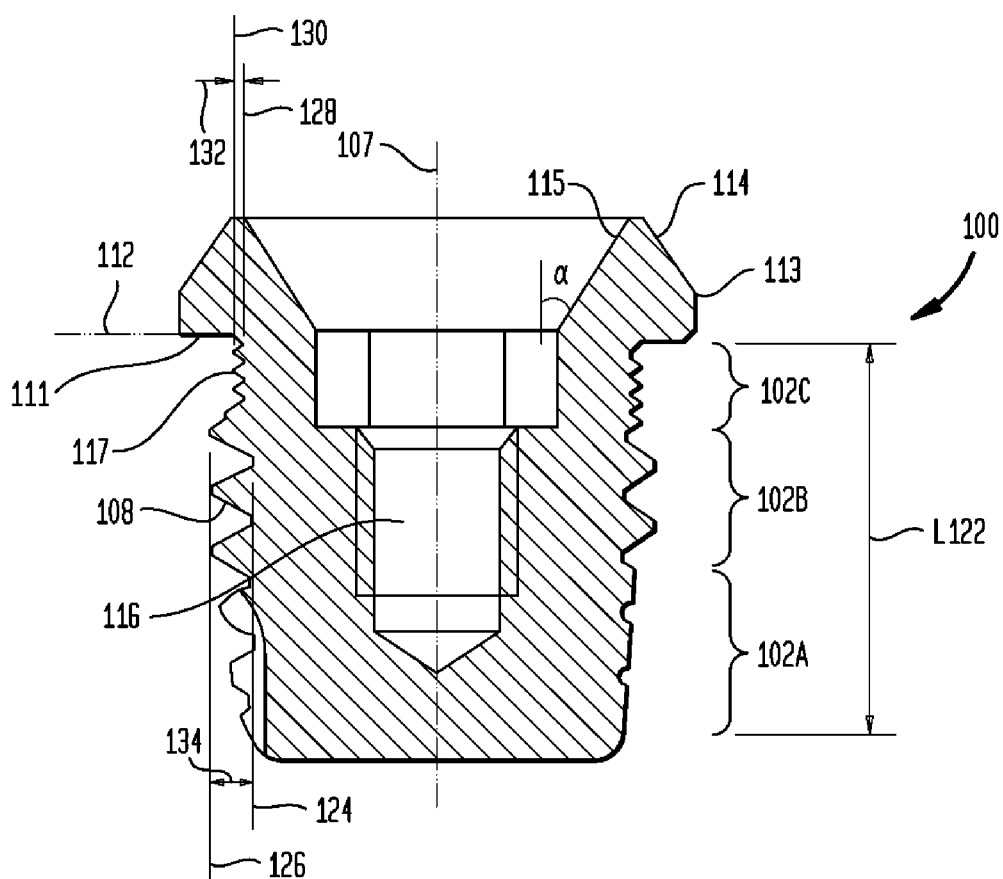
FIG. 2 is a cross-sectional side view of the anchoring element illustrated in FIG. 1.

The main body 102 has a length sufficient to securely anchor fixture 100 into, without penetrating entirely through, the skull bone. The length of main body 102 may therefore depend on the thickness of the skull bone at the implantation site. In one embodiment, main body 102 has a length (L) 122 no greater than approximately 5 mm. Main body 102 further comprises a distal tapered apical portion 102A and a straight, generally cylindrical body comprising two portions, a first portion 102B and a second portion 102C. First portion 102B comprises external threads that form the main screw thread 108 adjacent to the distal tapered apical portion. The second portion 102C is adjacent to the flange. As illustrated in FIG. 2, main screw thread 108 has an inner diameter 124 and an outer diameter 126. In one embodiment, the outer diameter 126 is approximately 3.5-5.0 mm.

As further shown in FIGS. 1 and 2, the distal tapered apical part 102A of main body 102 is configured with self-tapping cutting edges 109. Additional information regarding the self-tapping action is described in greater detail in WO 02/09622, which is hereby incorporated by reference herein. Clearance or relief surfaces 110 may also be provided, wherein the self-tapping cutting edges 109 and the clearance or relief surfaces 110 are provided in an alternating configuration around the main body periphery. This alternating configuration is advantageous because it creates more volume for the cut-off bone chips and therefore reduces the squeezing effect between the fixture 100 and the bone during installation.

As more clearly illustrated in FIG. 2, flange 103 has a planar bottom surface 111 for resting against the outer bone surface, indicated by 112, when the fixture 100 has been screwed into the skull bone. Again, flange 103 prevents the fixture 100 from completely penetrating through the skull bone. Preferably, flange 103 has a diameter which exceeds the peak diameter of the threads by approximately 10-20%. The outer peripheral surface of the flange has a cylindrical part 113 and a tapered top portion 114. The upper end of the flange is designed with an open cavity with a tapered inner side wall 115, a grip section 105, and an inner bottom bore 116 with an internal screw thread for directly or indirectly connecting a hearing aid device or any orbital or ear prosthesis. In order to achieve a stable connection, the inner opening and bore extends to the bottom half of the main body of the fixture 100. The tapered inner side wall 115 forms a seat for a skin-penetrating abutment or the like to create a good connecting fit between the two parts fixture and abutment. The cone angle α may be in the range of about 30-40 degrees. However, the connection with abutment and other parts in the system are not part of this invention and will not be described in any detail here.

In one embodiment, no protruding hex is provided in the embodiment depicted in FIGS. 1 and 2. Rather, the flange forms a smooth, open upper end. The smooth upper end of flange 103 and the absence of any sharp corners provides for improved soft tissue adaptation. Flange 103 also comprises a cylindrical part 113 and a flared top portion 114 which provide sufficient height in the longitudinal direction for internal connection with an abutment sleeve (not shown).

FIG. 2 shows the second portion 102C adjacent to flange 103 having an inner diameter 128 which exceeds the inner diameter 124 of the main threads 108 of the first portion 102B. As noted, this configuration provides a radial compression to the surrounding bone. Preferably the second portion 102C is provided with circumferential grooves 117, having an inner diameter 128 and an outer diameter 130. A drill may then be used having a diameter that is greater than the inner diameter 124 of screw thread 108 of first portion 102B, but less than the outer diameter 130 of second portion 102C of the cylindrical main body of the fixture, that is, 124<Drill Diameter<130. When fixture 100 is inserted into the drilled hole, the second portion 102C compresses the bone to some extent to impart initial stability. The wide diameter portion is located next to the flange so that the compressive action is more concentrated to the hard cortical part of the skull bone tissue.

As mentioned and illustrated in FIGS. 1 and 2, second portion 102C is preferably provided with circumferential grooves 117. In one embodiment, the inner diameter 128 also exceeds the inner diameter 124 of screw thread 108 of first portion 102B. Preferably the height 132 of the groove (130−128=132) is approximately ⅓ or less than the height of screw thread 108 of first portion 102B. In addition to the noted compressive action, such grooves may provide an increased retention between the fixture and the surrounding bone tissue, and spread the forces directed to the abutment more evenly in the bone.

This retention may also be improved by increasing the surface roughness of the bone contacting surfaces of fixture 100. For instance the surface may be modified by means of an abrasive blasting process according to WO 92/05745. In one embodiment the process is used to provide an average surface roughness Sa of about 0.2-2.0 μm, preferably 0.8-1.2 μm, and Sdr(2d/3d)=8-60%, preferably approximately 20-60%.

Circumferentially oriented grooves 117 may extend completely or partly around the periphery of the main body. In the embodiment shown in FIGS. 1 and 2 there are three separate grooves as an example. As an alternative, the grooves may be formed as a screw thread, which may have the same pitch as main screw thread 108, but having a inner diameter 128 that is greater than the inner diameter 124 of main screw thread 108, so that the height of the grooves 117 would be only approximately ⅓ or less of the height 134 of main screw thread 108 (126−124=134). In one embodiment, the extension of the second wide diameter portion 102C in the longitudinal direction of the fixture is about 15-25% of the total height of the fixture.

A method for inserting the fixture may comprise providing the anchoring fixture, drilling a hole, and inserting the anchoring fixture into the hole until the flange contacts the skull bone, wherein the hole has a diameter that is greater than the inner diameter of the first portion and less than the outer diameter of the second portion. No countersinking or removal of cortical bone is used which leaves more good bone left. When fixture 100 is inserted into such a drilled hole, the wider second portion of the fixture, that is, portion 102C next to the flange, provides a certain compression of the cortical bone on the radial direction of the prepared bone hole.

Further features and advantages of the present invention may be found in U.S. Provisional Application No. 60/951, 169, entitled "Coupling Apparatus For a Bone Anchored Hearing Device," and filed Jul. 20, 2007, and U.S. Provisional Application No. 60/951,163, entitled "Bone Anchor Fixture for a Medical Prosthesis," and filed Jul. 20, 2007, which are hereby incorporated by reference herein.

The invention is not limited to the embodiment illustrated in the drawings but may be varied within the scope of the accompanying claims. Specifically, it is understood that other types of abrasive methods, coatings etc, may be used for increasing the roughness of bone-contacting surfaces. Such methods are known per se and not described here in any detail.

What is claimed is:

1. An anchoring fixture, comprising:
   a screw thread apparatus including a screw thread having a varying outer diameter, wherein
   the anchoring fixture is configured for anchoring a bone conduction hearing prosthesis component to a skull bone at a location behind an external ear so that sound is transmitted from the bone conduction hearing prosthesis component via the skull bone to a cochlea,
   a maximum diameter of the anchoring fixture has a value that exceeds a peak diameter of the screw thread by approximately 10-20%,
   a length in a direction along a longitudinal axis of the anchoring fixture from (i) a distal end of the anchoring fixture to (ii) a distalmost portion of the anchoring fixture that exceeds the peak diameter of the screw thread by approximately 10-20%, is no greater than 5 mm, the screw thread apparatus being between the distal end and a proximal end of the anchoring fixture, the proximal end facing away from the skull bone when the anchoring fixture is implanted in the skull bone, and
   a maximum diameter of the screw thread apparatus is between 3.5 and 5 mm.

2. The anchoring fixture of claim 1, wherein:
   a portion of a surface of the anchoring fixture that contacts the skull bone has a modified increased surface roughness relative to another portion of the surface of the anchoring fixture that contacts the skull bone.

3. The anchoring fixture of claim 1, wherein:
   a portion of the anchoring fixture between the proximal end and the distal end has a wide diameter portion configured to result in a compressive action that is more concentrated to a hard cortical part of skull bone tissue when the bone fixture is fully seated in the skull bone.

4. The anchoring fixture of claim 1, wherein:
   a portion of a surface of the anchoring fixture that contacts the skull bone has a modified increased surface roughness relative to another portion of the surface of the anchoring fixture that contacts the skull bone; and
   a portion of the anchoring fixture between the proximal end and the distal end has a wide diameter portion configured to result in a compressive action that is more concentrated to a hard cortical part of skull bone tissue when the bone fixture is fully seated in the skull bone.

5. The anchoring fixture of claim 3, wherein:
   the wide diameter portion is configured to exert the compressive action onto the skull bone in a radial direction, to stabilize the bone fixture in the skull bone, when the bone fixture is implanted.

6. The fixture of claim 1, wherein:
   the anchoring fixture has an area having a diameter that is greater than a maximum inner diameter of the screw thread, the area being configured to exert a compression force onto the skull bone in a radial direction, thereby stabilizing the anchoring fixture in the skull bone when implanted therein.

7. The anchoring fixture of claim 1, further comprising:
   means for exerting a compression onto the skull bone in a radial direction concentrated at a cortical part of the bone to stabilize the bone fixture in the skull bone.

8. A bone conduction hearing prosthesis anchoring fixture, comprising:
   a main body including a threaded section configured to be implanted into a skull bone, and
   a proximal portion, the proximal portion being located above the main body when the anchoring fixture is implanted into the skull bone, wherein
   the bone conduction hearing prosthesis anchoring fixture is configured for anchoring a bone conduction hearing prosthesis component to the skull bone at a location behind an external ear so that sound is transmitted from the bone conduction hearing prosthesis component via the skull bone to a cochlea, and a portion of the bone conduction hearing prosthesis anchoring fixture main body between a proximal end at the proximal portion and a distal end opposite the proximal end of the bone conduction hearing prosthesis anchoring fixture has a wide diameter portion configured to impart a compressive action that is concentrated to a hard cortical part of skull bone tissue when the bone conduction hearing prosthesis anchoring fixture is fully seated in the skull bone, wherein the wide diameter portion is configured to exert the compressive action onto the skull bone in a radial direction.

9. The bone conduction hearing prosthesis anchoring fixture of claim 8, wherein:

the bone conduction hearing prosthesis anchoring fixture is configured to prevent the main body from completely penetrating through the skull bone.

10. The bone conduction anchoring fixture of claim 8, wherein:

the bone conduction hearing prosthesis anchoring fixture includes a head that has a diameter measured normal to a longitudinal axis of the fixture that exceeds a peak diameter of a screw thread of the threaded section by at least approximately 10%.

11. The bone conduction hearing prosthesis anchoring fixture of claim 8, wherein:

the wide diameter portion is configured to exert the compressive action onto the skull bone in the radial direction to stabilize the bone fixture in the skull bone, when the bone fixture is implanted.

12. The bone conduction hearing prosthesis anchoring fixture of claim 8, wherein:

a portion of a surface of the bone conduction hearing prosthesis anchoring fixture that contacts the skull bone has a modified increased surface roughness relative to another portion of the surface of the bone conduction hearing prosthesis anchoring fixture that contacts the skull bone.

13. The bone conduction hearing prosthesis anchoring fixture of claim 8, wherein:

the wide diameter portion is a means for exerting a compression onto the skull bone in the radial direction to stabilize the fixture in the skull bone; and
the fixture includes titanium.

14. The bone conduction hearing prosthesis anchoring fixture of claim 8, wherein:

the threaded section includes a screw thread;
the anchoring fixture includes a fixture head; and
a section between the threaded section and the head includes a recessed portion that extends about the bone conduction hearing prosthesis anchoring fixture at a constant location relative to a location along a longitudinal axis of the bone conduction hearing prosthesis anchoring fixture, the recessed portion being a portion of smallest diameter between the threaded section and the head, the recessed portion spanning a distance in a direction of the longitudinal axis a distance less than a pitch of the screw thread of the threaded section.

15. A method, comprising:

drilling a hole into a skull bone at a location behind an external ear of a person;
obtaining an anchoring fixture for anchoring a prosthesis to a skull bone, the anchoring fixture including:
a main body configured to be implanted into the skull bone, the main body comprising a screw thread apparatus including a screw thread, the main body having a taper, wherein a first portion of the main body has a first inner diameter and a second portion of the main body has a second inner diameter,
the second portion is located closer to a proximal end of the bone fixture than the first portion,
a maximum diameter of the screw thread is greater than a length of the screw thread apparatus, and
the anchoring fixture is configured for anchoring a hearing prosthesis component to the skull bone at the location behind the external ear so that sound is transmitted from the hearing prosthesis via the skull bone to a cochlea; and inserting the anchoring fixture to the hole such that the proximal end faces away from the skull bone.

16. The method of claim 15, wherein:

the action of inserting the anchoring fixture into the hole results in certain compression to the skull bone in the radial direction to provide initial stability of the bone fixture.

17. The method of claim 16, wherein:

the certain compression to the skull bone is concentrated to the hard cortical part of the skull bone.

18. The method of claim 15, wherein:

the hole has a diameter that is greater than an inner diameter of screw thread of the first portion of the bone fixture but less than an outer diameter of the second portion of the bone fixture.

19. The method of claim 18, wherein:

the action of inserting the anchoring fixture into the hole results in certain compression to the skull bone in the radial direction to provide initial stability of the bone fixture.

20. The method of claim 19, wherein:

the certain compression to the skull bone is concentrated to the hard cortical part of the skull bone.

21. The method of claim 20, wherein:

the difference between the diameter of the hole and the inner diameter of the screw results in the certain compression.

22. The anchoring fixture of claim 3, wherein:

the wide diameter portion is configured to exert the compressive action onto the skull bone in a radial direction.

23. The bone conduction hearing prosthesis anchoring fixture of claim 8, wherein:

the threaded section includes a screw thread; and
the main body includes a fixture head configured to prevent the main body from completely penetrating through the skull bone.

24. The bone conduction hearing prosthesis anchoring fixture of claim 8, wherein:

the threaded section includes a screw thread; and
the main body has a section that is the maximum diameter of the anchoring fixture as measured normal to a longitudinal axis of the anchoring feature; and
the section is located above the wide diameter portion when the anchoring fixture is implanted into the skull bone.

25. The bone conduction hearing prosthesis anchoring fixture of claim 8, wherein:

the wide diameter portion is configured to extend into the skull bone when the anchoring fixture is implanted into the skull bone.

26. The bone conduction hearing prosthesis anchoring fixture of claim 8, wherein:

the anchoring fixture includes a section that has a wider diameter than the wide diameter portion.

* * * * *